United States Patent
López Zarco et al.

(10) Patent No.: US 9,662,369 B2
(45) Date of Patent: May 30, 2017

(54) USE OF A CASEIN HYDROLYSATE AS AN ANTIHERPETIC AGENT

(71) Applicant: NTD Labs, S.L., Terrassa (ES)

(72) Inventors: Guillermo López Zarco, Terrassa (ES); Pere Adell Winkler, Terrassa (ES)

(73) Assignee: NTD Labs, S.L., Terrassa (ES)

( * ) Notice: Subject to any disclaimer, the term of this patent is extended or adjusted under 35 U.S.C. 154(b) by 0 days.

(21) Appl. No.: 14/422,951

(22) PCT Filed: Aug. 21, 2013

(86) PCT No.: PCT/IB2013/056775
§ 371 (c)(1),
(2) Date: Feb. 20, 2015

(87) PCT Pub. No.: WO2014/030125
PCT Pub. Date: Feb. 27, 2014

(65) Prior Publication Data
US 2015/0343010 A1 Dec. 3, 2015

(30) Foreign Application Priority Data

Aug. 23, 2012 (ES) .................................. 201231324

(51) Int. Cl.
*A61K 38/01* (2006.01)
*A61K 9/00* (2006.01)

(52) U.S. Cl.
CPC ............ *A61K 38/018* (2013.01); *A61K 9/009* (2013.01); *A61K 9/0014* (2013.01); *A61K 9/0053* (2013.01); *A61K 38/017* (2013.01)

(58) Field of Classification Search
None
See application file for complete search history.

(56) References Cited

U.S. PATENT DOCUMENTS

| | | | |
|---|---|---|---|
| 5,859,187 A | 1/1999 | Matthews et al. | |
| 2005/0148504 A1* | 7/2005 | Katunuma | |
| 2009/0311236 A1 | 12/2009 | Kochel et al. | |
| 2011/0165306 A1* | 7/2011 | Dekker .................... | C12N 9/58 426/590 |

FOREIGN PATENT DOCUMENTS

| | | |
|---|---|---|
| DE | 3922453 | 1/1991 |
| EP | 0246630 | 11/1987 |
| EP | 0292255 | 11/1988 |
| GB | 2185024 | 7/1987 |
| WO | WO-92/14751 | 9/1992 |
| WO | WO-92/17191 | 10/1992 |
| WO | WO-93/21941 | 11/1993 |
| WO | WO-95/15766 | 6/1995 |
| WO | WO-98/04707 | 2/1998 |
| WO | WO-01/57072 | 8/2001 |
| WO | WO-02/45524 | 6/2002 |
| WO | WO 2006/000350 | * 1/2006 |
| WO | WO-2006/000350 | 1/2006 |
| WO | WO-2006/018431 | 2/2006 |
| WO | WO-2007/016450 | 2/2007 |

OTHER PUBLICATIONS

Demaubeuge, et al., Thymopentin treatment of herpes simplex infections. An open, monitored, multicenter study, *Surv. Immunol.* vol. 4 Suppl. 1 1985, 30-36.
Floris, et al., Antibacterial and Antiviral Effects of Milk Proteins and Derivatives Thereof, *Current Pharmaceutical Design*, Bentham Science Publishers, NL vol. 9 No. 16 Jan. 2003, 1257-1275.
Gaby, Alan R., Natural Remedies for Herpes simplex, *Alternative Medicine Review* vol. 11 No. 2 Jun. 2006, 93-101.
Jensen, H., Antimicrobial activity of lactoferrin and lactoferrin derived peptides, *Dietary Protein Research Trends*, J. R. Ling, editor, Nova Science Publishers, New York 2007, 1-62.
PCT International Search Report in PCT/IB2013/056775, mailed Feb. 24, 2014, 5 pages.
PCT International Written Opinion in PCT/IB2013/056775, mailed Feb. 24, 2014, 5 pages.
PCT International Preliminary Report on Patentability in PCT/IB2013/056775, dated Feb. 24, 2015, 6 pages.

* cited by examiner

*Primary Examiner* — James H Alstrum Acevedo
*Assistant Examiner* — Roy Teller
(74) *Attorney, Agent, or Firm* — Servilla Whitney LLC

(57) ABSTRACT

The present invention relates to the use of a casein hydrolysate as an antiherpetic agent. This casein hydrolysate has an application in both the treatment and the prevention of the reactivation of a latent infection by a herpesvirus, and is effective both orally and topically. It also relates to a pharmaceutical composition in the form of cream, gel, ointment or paste for topical administration that contains it.

12 Claims, No Drawings

USE OF A CASEIN HYDROLYSATE AS AN ANTIHERPETIC AGENT

CROSS-REFERENCE TO RELATED APPLICATIONS

This is the National Phase entry of International Patent Application No. PCT/IB2013/056775, filed Aug. 21, 2013, which claims priority to Spanish Patent Application No. 201231324, filed Aug. 23, 2012, the disclosures of which are incorporated herein by reference in their entireties.

REFERENCE TO SEQUENCE LISTING

The material contained in the text file identified as "ING0004-00US_ST25.txt" (created Aug. 19, 2015, 4.9 KB) is hereby incorporated by reference.

TECHNICAL FIELD

The present invention relates to products for the treatment and prevention of viral diseases caused by herpesvirus.

BACKGROUND ART

Herpesviruses are responsible for a large number of diseases, which can affect different collectives at a greater or lesser extent and that can become particularly severe in immunocompromised subjects such as, for example, premature infants, elders, transplanted patients or patients infected with the human immunodeficiency virus (HIV). Oral and genital infections by herpesvirus are of special relevance.

Herpesviruses belong to the family of Herpesviridae and are DNA type virus. They are constituted by a DNA chain surrounded by an icosahedral capsid, which, in turn, is surrounded by a tegument and a membrane disposed as a coating.

Eight different species have been identified among the herpesviruses: herpes simplex virus type (HSV-1), type 2 (HSV-2), varicella zoster virus (VZV), Epstein-Barr virus (EBV), cytomegalovirus (HCMV) and herpesvirus type 6 (HHV-6), 7 (HHV-7) and 8 or Kaposi's Sarcoma herpesvirus (HHV-8, KSHV).

All of them share the common feature that, after infection, they may remain in a latent state, alternating latent periods with reactivation periods throughout the whole life of the infected individual. The latent period is characterized by a minimal expression of the viral gene and the absence of synthesis of new viruses.

Usually a distinction can be drawn between primary infection, referred to the first infection of the subject by the virus, which usually occurs in childhood or adolescence and which is often asymptomatic, and the subsequent reactivations which lead to recurrent injuries. These reactivations occur in an unpredictable way, but there exist some triggering factors, such as illnesses, physical or mental stress situations, hormonal changes, ultraviolet radiation, or corticoids use, among others. Both primary and recurrent infections can be relatively mild, but under certain circumstances they can become fatal to the host.

Diseases caused by herpesvirus infection are diverse due to the variety of the viruses and also because most of them can interact with the infected patient in more than one way and cause more than one pathology.

Thus, for example, the VZV virus is the responsible for varicella as a primary infection, whereas the reactivation of the latent virus in adults leads to herpes zoster. Herpes zoster affects the peripheral nerves and the skin, and can show serious complications, especially in individuals with alterations in their immune system.

EBV virus is the cause of infectious mononucleosis, particularly in teenagers. The EBV latent infection can be reactivated, especially in HIV-positive patients, resulting in the hairy leukoplakia. Also, the infection by said virus can lead to malignant lesions such as nasopharyngeal carcinoma, Burkitt's lymphoma, B cell lymphoma or oral carcinoma.

Cytomegalovirus infection can lead to the perinatal disease, acute HCMV infection, and to the worsening of opportunistic infections in immunocompromised patients, e.g. transplanted patients or HIV infected patients.

The most frequent herpesviruses are herpes simplex HSV-1 and HSV-2, which are responsible for a large variety of infections involving vesicular eruptions on the skin and mucous membranes, and that can also occasionally affect the central nervous system and visceral organs.

HSV-1 infection is mainly associated with the orofacial region, causing infections from mild, such as herpes labialis, to severe, such as viral encephalitis. The most common injury associated with HSV-1 is the herpes labialis, although it can also cause other pathologies such as, for example, primary herpetic gingivostomatitis, recurrent intraoral herpes and ocular herpes simplex.

HSV-2 causes injuries that are similar to oral herpes, but which occur mainly in the genital region (genital herpes), although it may also be involved in herpes labialis. HSV-2 infection can be transmitted to newborns during delivery, so that a significant percentage of infants born from women with genital herpes become infected with HSV-2, and many of them suffer serious defects induced by the virus. The genital herpes has been associated with an increased risk of HIV transmission, and vice versa, due to the presence of genital ulcers.

Exceptionally, the reactivation or primary infection with herpes simplex virus can cause other serious and high mortality diseases, such as pneumonitis, hepatitis, tracheobronchitis or disseminated infection.

At present, the most widely used therapy for treating herpesvirus infections is aciclovir, particularly for genital herpes, herpes labialis or herpes zoster, and it may be administered topically, orally or intravenously, depending on the type and severity of the pathology. Other antivirals that are also used as antiherpetics are, for example, valaciclovir, famciclovir, penciclovir, ganciclovir, foscarnet, and cidofovir, among others.

These drugs are not actually a cure that completely eliminates the herpesvirus infection from the organism, but rather they are used to mitigate the infection outbreaks, to help to reduce the pain and to make the symptoms disappear faster.

However, none of these drugs has proved to be totally effective. Furthermore, all of them involve certain side effects. For example, locally administered aciclovir can cause irritation and burning, while when it is administered orally, it can sometimes lead to gastrointestinal disorders, headache and less frequently, renal failure or neurotoxicity.

Moreover, the continued use of antiviral drugs may cause resistances, and a lack of efficacy in the long term. That is why it is necessary to provide new alternative drugs for the treatment of herpesvirus infections, which are safe and do not cause undesirable side effects.

In this regard, in the prior art there have been disclosed different approaches for the treatment of infections caused by herpesviruses, with less side effects, using therapies of natural origin based on the administration of certain amino acids and/or peptides.

Thus, for example, in the article A. R. Gaby, *Natural Remedies for Herpes simplex*, Altern. Med. Rev, 2006, 11 (2), 93-101, some alternative or complementary therapies to aciclovir are mentioned for the treatment of herpes simplex infections, among them the treatment with the amino acid lysine, which exerts an antagonistic mechanism on arginine, which is an amino acid required for the replication of herpes simplex virus.

The international patent application WO-A-2007/016450 relates to the use of the amino acid glutamine, or its analogues, conjugates and derivatives for the treatment or prevention of the reactivation of herpes infections, for example those caused by HSV-1 and HSV-2. Although this document relates mainly to the amino acid glutamine as such, short peptides containing glutamine are also included, for example, Gly-Gln, Ala-Gln or Gly-Gly-Gln.

In the book chapter H. Jensen, *Antimicrobial activity of lactoferrin and lactoferrin derived peptides*, in: *Dietary Protein Research Trends*, J. R. Ling, editor, Nova Science Publishers, New York, 2007, Chapter 1, pages 1-62, it is described how lactoferrin protein present in the milk serum, as well as some specific peptides derived therefrom, have antiviral activity against, among others, the HSV-1 and HSV-2 viruses.

In the German patent application DE-A-3922453 an extract prepared from a hydrolysate of the milk serum proteins is disclosed, which has antiherpetic properties. The proteins from which the hydrolysate is prepared can be alpha-lactalbumin, lactoferrin, beta-lactoglobulin, lysozyme, or serum albumin, all of them present in the milk serum. First, these proteins are hydrolysed with at least one protease, for example, papain, pancreatin or chymotrypsin, and the residue obtained is extracted with a nonpolar solvent such as petroleum ether, benzene or toluene.

In the international patent application WO-A-92/17191 it is disclosed the use of the dipeptide L-Glu-L-Trp, called Thymogen®, for the treatment, in general, of opportunistic infections in immunocompromised patients, and in particular also for the treatment of herpes.

In the prior art, many specific peptides have been disclosed, having different sequences, which have activity against herpes viruses. Its structure is often derived from certain viral proteins responsible for the replication of herpes virus.

Thus, in the article DeMaubeuge et al, *Thymopentin treatment of herpes simplex infections. An open, monitored, multicenter study*, Surv. Immunol., 1985, 4 (Suppl.1), 30-36, a clinical study is disclosed with patients suffering from herpes labialis and genital herpes, to whom the thymopentin product was administered subcutaneously, so that a clear improvement was observed. Thymopentin is a pentapeptide with immunoregulatory properties whose sequence (Arg-Lys-Asp-Val-Tyr; SEQ ID NO:1) corresponds to the residues 32-36 of the protein thymopoietin.

In the British patent GB-A-21 85024, peptides inhibitors of the enzyme ribonucleotide reductase are disclosed, which contain a portion of the sequence of this enzyme, and which exhibit antiviral activity against herpesviruses. Among them the following peptides are disclosed: $NH_2$-Tyr-Gly-Ala-Val-Val-Asn-Asp-Leu-COOH (SEQ ID NO:2), and $NH_2$-Tyr-Ala-Gly-Ala-Val-Val-Asn-Asp-Leu-COOH (SEQ ID NO:3).

In the European patent application EP-A-0246630 certain peptide structures are disclosed such as, for example, the nonapeptide having the sequence H-Tyr-Ala-Gly-Ala-Val-Val-Asn-Asp-Leu-OH (SEQ ID NO:4), which possesses antiviral activity against herpes simplex virus.

In European patent application EP-A-0292255 it is disclosed that the pentapeptide Val-Val-Asn-Asp-Leu (SEQ ID NO:5) has antiviral activity, and that other larger peptides, which contain this specific sequence, also show the same activity.

The U.S. Pat. No. 5,859,187 relates to peptides with antiviral activity, based on fragments of the amino acid sequence of the enzyme DNA polymerase of the HSV, which are able to inhibit the activity of this enzyme. The preparation of several peptides is disclosed as, for example, H-Ala-Pro-Gly-Asp-Glu-Pro-Ala-Pro-Pro-Tyr-$NH_2$ (SEQ ID NO:6).

In the international patent application WO-A-92/14751 a series of peptides are disclosed with activity against the virus HSV-1 and HSV-2, varicella zoster virus, human cytomegalovirus or Epstein-Barr virus. Among them, the following peptides are disclosed as particularly preferred D-Ala-Ser-Thr-Thr-Thr-Asn-Tyr-Thr-$NH_2$ (SEQ ID NO:7), Ala-Ser-Thr-Thr-Thr-Asn-Tyr-Thr (SEQ ID NO:8), D-Ala-Ser-Thr-Thr-Thr-Asn-Tyr-Thr (SEQ ID NO:9), D-Ala-Ala-Ser-Ser-Ser-Asn-Tyr-Met (SEQ ID NO:10), Thr-Asp-Asn-Tyr-Thr (SEQ ID NO:11), Thr-Thr-Ser-Tyr-Thr (SEQ ID NO:12), Thr-Thr-Asn-Tyr-Thr (SEQ ID NO:13).

In the international patent application WO-A-93/21941, peptides comprising at least 6 amino acid residues are disclosed, which have activity against herpes simplex virus thanks to their ability to inhibit its replication. Preferably, the amino acids are in the (D) configuration and the following peptides are particularly highlighted: D-[Arg-Lys-Lys-Arg-Arg-Gln-Arg-Arg-Arg] (SEQ ID NO:14), D-[Arg-Arg-Arg-Arg-Arg-Arg-Arg-Arg-Arg] (SEQ ID NO:15) and D-[Arg-Arg-Arg-Gln-Arg-Arg-Arg-Arg-Arg] (SEQ ID NO:16). These products are preferably administered by injection, as well as topically or orally.

In the international patent application WO-A-95/1 5766 peptide derivatives with antiviral activity are disclosed, which consist of seven amino acids, including the following sequence: Arg-Arg-Trp-Trp-Cys-Arg-X (SEQ ID NO:17), where X is an amino acid or an amino acid derivative that contains a chiral center.

In the international patent application WO-A-98/04707 some antiviral agents are disclosed showing a mechanism based on preventing the association between two viral proteins required for the DNA replication of HSV virus. Several peptide sequences are disclosed, corresponding to a portion of the protein UL8 of HSV-1 virus, for example, IELVFTGVLAGVWGEGGKFV (SEQ ID NO:18).

In the international patent application WO-A-01/57072 some peptides with the capacity of crossing lipid membranes are disclosed, which exhibit antiviral activity against herpes simplex virus. Several sequences that show such activity are cited, for example, $NH_2$-RRKKAAVALLPAVLLALLAP-COOH (SEQ ID NO:19).

In the international patent application WO-A-2006/0 18431 it is disclosed that the peptide designated as Hervip, which consists in the amino acid sequence 112-147 of human β-hemoglobin, has activity against herpes simplex virus. This peptide corresponds to the following sequence of 35 amino acids: $NH_2$-VCVLAHHFGKEFTPPVQAAYQK-WAGVANALAHKYH-COOH (SEQ ID NO:20).

In view of the wide variety of solutions described in the prior art regarding the use of peptides in the prevention and/or treatment of the infections caused by herpesviruses, it appears that a satisfactory solution has not yet been found.

Thus, there remains a need to develop new compositions and methods for treating herpesvirus infections which are effective and practical, and that are also safe, so that they involve a minimal risk of side effects.

OBJECT OF THE INVENTION

The object of the present invention is the use of a casein hydrolysate as antiherpetic.

It is also a part of the object of the invention a pharmaceutical composition for topical administration comprising such hydrolysate.

DETAILED DESCRIPTION OF THE INVENTION

The object of the present invention is the use of a casein hydrolysate for the preparation of a medicament for the prevention and/or treatment of infections caused by herpesvirus, wherein the hydrolysate comprises peptides wherein the molar fraction of peptides carrying a carboxy terminal proline, expressed in %, is more than two times the molar fraction of proline, expressed in %, in the casein substrate used to generate the hydrolysate.

That is, the object of the invention is a casein hydrolysate for use in the prevention and/or treatment of infections caused by herpesvirus, wherein the hydrolysate comprises peptides wherein the molar fraction of peptides carrying a carboxy terminal proline, expressed in %, is more than two times the molar fraction of proline, expressed in %, in the casein substrate used to generate the hydrolysate.

The authors of the present invention have observed that, surprisingly, the casein hydrolysate of the invention is extremely effective for achieving a rapid remission of the outbreaks by reactivation of the herpes virus infections, as well as for preventing or minimizing the appearance of new manifestations of the infection.

Casein Hydrolysate

The name casein includes a group of phosphoproteins present in the milk, which represents approximately a 3% of the bovine milk. The main components of casein are alpha-, beta-, gamma- and kappa-caseins, among which beta casein is the major fraction of bovine milk.

The casein used as substrate for the hydrolysis is preferably casein from bovine milk, more preferably beta-casein from bovine milk.

The casein hydrolysate used as antiherpetic according to the use of the present invention, is a hydrolysate whose composition is determined by the use of a proline specific endoprotease in the hydrolysis of the casein, so that the hydrolysate has a composition characterized by a high content of peptides with a proline at the carboxy-terminal end.

In the use of the invention, the molar fraction of the peptides in such hydrolysate carrying a carboxy terminal proline, expressed in %, is more than two times the molar fraction of proline, expressed in %, in the casein substrate used to generate hydrolysate.

The characteristics of this hydrolysate and of the proline specific endopeptidase used in its preparation are described in the international patent application WO-A-02/45524. In that document it is also disclosed the method for determining the molar fraction of the peptides carrying a carboxy terminal proline, expressed in %, as well as the method for determining the molar fraction of proline, expressed in %, in the casein substrate used to generate the hydrolysate.

In this patent application it is disclosed the preparation of protein hydrolysates with a high ratio of proline residues in the carboxyl-terminal position, in the context of the preparation of dietetic protein supplements, especially for sport drinks, with the advantage that such composition has an improved taste, free from the characteristic bitter taste that usually exhibit many of these hydrolysates.

The authors of the present invention have found that, surprisingly, this casein hydrolysate exhibits an excellent therapeutic activity against herpesvirus infections.

Preferably, the molar fraction of the peptides of this hydrolysate carrying a carboxy terminal proline, expressed in %, is at least three times the molar fraction of proline, expressed in %, in the casein substrate used to generate the hydrolysate.

Preferably, in the casein hydrolysate according to the use of the present invention, the average length of the peptides in the hydrolysate is comprised between 3 and 9 amino acids.

Preferably, the molar fraction of peptides carrying a carboxy terminal proline in the casein hydrolysate is at least 25%, and still more preferably it ranges between 30% and 70%.

Within the context of the present invention, when discussing the molar fraction of peptides, peptides are understood to be those whose molecular mass ranges between 400 and 2000 Dalton, which can be determined, for example, using the liquid chromatography/mass spectrometry (LC/MS) method described in the Materials and Methods section of the international patent application WO-A-02/45524 cited above.

In general, the casein hydrolysate according to the use of the present invention is a hydrolysate where at least the 50% of the casein substrate is hydrolysed. Preferably at least a 10% of the casein substrate is converted into peptides with a molecular mass between 400 and 2000 Dalton, more preferably, between 20% and 90%, and still more preferably between 30% and 80% of the casein substrate is converted into such peptides.

In a preferred embodiment the casein hydrolysate has the following amino acid composition: between 54-64 of lysine, between 22-30 of methionine, between 25-33 of threonine, between 18-26 of histidine, between 26-34 of arginine, between 46-56 of valine, between 34-42 of isoleucine, between 70-80 of leucine, between 33-41 of phenylalanine, between 45-55 of the sum of aspartic acid plus asparagine, between 160-180 of the sum of glutamine plus glutamic acid, between 20-26 of alanine, between 80-90 of proline, between 40-48 of tyrosine, between 37-45 of serine, between 11-17 of glycine, between 0.8-1.2 of cysteine, and between 6-10 of tryptophan; wherein the amounts are expressed in grams of each amino acid per kilogram of hydrolysate.

In a more preferred embodiment the casein hydrolysate has the following amino acid composition: between 57-61 of lysine, between 24-28 of methionine, between 27-31 of threonine, between 20-24 of histidine, between 28-32 of arginine, between 49-53 of valine, between 36-40 of isoleucine, between 73-77 of leucine, between 35-39 of phenylalanine, between 48-52 of the sum of aspartic acid plu asparagine, between 166-176 of the sum of glutamine plus glutamic acid, between 21-25 of alanine, between 82-88 of proline, between 42-46 of tyrosine, between 39-43 of serine, between 13-15 of glycine, between 0.8-1.2 of cysteine and between 7-9 of tryptophan; wherein the amounts are expressed in grams of each amino acid per kilogram of hydrolysate.

In a particularly preferred embodiment the casein hydrolysate has approximately the following amino acid composition: 59 of lysine, 26 of methionine, 29 of threonine, 22 of histidine, 30 of arginine, 51 of valine, 38 of isoleucine, 75 of leucine, 37 of phenylalanine, 50 of the sum of aspartic acid plus asparagine, 171 of the sum of glutamine plus glutamic acid, 23 of alanine, 85 of proline, 44 of tyrosine, 41 of serine, 14 of glycine, 1 of cysteine, and 8 of tryptophan; wherein the amounts are expressed in grams of each amino acid per kilogram of hydrolysate.

A casein hydrolysate according to the specified characteristics is available under the trademark PeptoPro® (DSM). According to its data sheet, this product has applications in food and beverages to enrich their protein content.

Use of the Casein Hydrolysate

The authors of the present invention have noticed that the casein hydrolysate according to the characteristics specified above shows excellent antiherpetic properties, being effective for the prevention and/or treatment of infections caused by herpesviruses.

The infections caused by herpesviruses, according to the use of the present invention, relate to the infections caused by any type of herpesvirus, in particular those caused by herpesviruses selected from the group consisting of herpes simplex type 1, herpes simplex type 2, varicella zoster virus, Epstein-Barr virus, cytomegalovirus, herpesvirus type 6, herpesvirus type 7, and Kaposi's Sarcoma herpesvirus; preferably herpes simplex type 1, herpes simplex type 2 and varicella zoster virus.

In a preferred embodiment, the use according to the present invention relates to the prevention and/or treatment of herpesvirus infections selected from the group consisting of herpes labialis, genital herpes, and herpes zoster.

Within the context of the present invention the term "treatment" refers to the administration of the product with a curative purpose, once some symptoms or external manifestations of the infection have been observed, such as pain, burning, inflammation or itching in the affected area, as well as the appearance of pustules, vesicles, blisters, or rash, for example, or other symptoms or specific manifestations for each type of particular pathology. The curative purpose of such treatment is understood as being directed to the elimination, alleviation, improvement, or lessening of the severity of the external manifestations of the infection. Habitually it is not strictly a cure meaning the eradication of the virus, as the herpesviruses usually remain in an asymptomatic latent state in the infected individuals throughout their lives, alternating with periods of reactivation. The curative purpose in this sense means the cure of the disease outbreaks which have appeared, in order to achieve their remission and the return of the infection to an asymptomatic latent state.

Within the context of the present invention the term "prevention" refers to the administration of the product when there are no symptoms or external manifestations of the infection, but it is administered with a prophylactic purpose with the intention of preventing or delaying the appearance of new outbreaks of the infection, i.e., keeping it in an asymptomatic latent state.

In Examples 3, 4 and 5 some efficacy trials performed with the casein hydrolysate are shown. In those examples the casein hydrolysate was administered to patients suffering from various types of herpes, and they all showed a great efficacy in the relief of symptoms (treatment) as well as in the disappearance or diminution of the reactivation phases (prevention).

As the product used in the present invention is completely harmless, derived from the hydrolysis of casein from bovine milk and commonly used as a dietetic supplement, the use according to the present invention has the advantage that it is possible to maintain a long preventive treatment, without the risk of experiencing undesirable side effects, as usually happens with other antiviral treatments, so that the patients taking preventative doses are able to remain without any outbreak of the disease for very long periods, as shown in these examples.

In a preferred embodiment, the use of the casein hydrolysate according to the invention is characterized in that the hydrolysate is administered orally.

In a more preferred embodiment, the casein hydrolysate is administered according to a daily oral dose comprised between 4 and 40 g. In a still more preferred embodiment, a unit oral dose comprised between 4 and 8 g of the casein hydrolysate is used, and more preferably comprised between 5.5 and 6.5 g, which is administered from 1 to 5 times daily, and more preferably from 1 to 3 times daily.

Generally within a period of one week, the symptoms of herpes remit completely. In the case of herpes labialis, usually, preferably within 2 to 3 days, and in the case of genital herpes and herpes zoster preferably within 4 to 6 days.

The casein hydrolysate can also be used preventively after the remission of the symptoms by taking a daily unit oral dose of between 4 and 8 g for a period ranging from 12 to 24 months.

In another preferred embodiment, the use of the casein hydrolysate according to the present invention is characterized in that the hydrolysate is administered topically, so that it is locally applied on the area affected by the lesion.

Preparations with the Casein Hydrolysate

The casein hydrolysate according to the use of the present invention typically comes in powder solid form and can be administered either directly or in combination with at least one pharmaceutically acceptable excipient and/or carrier, in the form of a pharmaceutical composition.

It is also part of the object of the present invention, the use of a casein hydrolysate for the preparation of a medicament for the prevention and/or treatment of infections caused by herpesvirus, characterised in that the casein hydrolysate is administered in the form of a pharmaceutical composition comprising a pharmacologically effective amount of this hydrolysate and at least one pharmaceutically acceptable excipient and/or carrier, wherein this hydrolysate comprises peptides wherein the molar fraction of peptides carrying a carboxy terminal proline, expressed in %, is more than two times the molar fraction of proline, expressed in %, in the casein substrate used to generate the hydrolysate.

I.e., it is also part of the object of invention a casein hydrolysate for use in the prevention and/or treatment of infections caused by herpesvirus, characterized in that the hydrolysate is administered in the form of a pharmaceutical composition comprising this casein hydrolysate and at least one pharmaceutically acceptable excipient and/or carrier, wherein this hydrolysate comprises peptides wherein the molar fraction of peptides carrying a carboxy terminal proline, expressed in %, is more than two times the molar fraction of proline, expressed in %, in the casein substrate used to generate the hydrolysate.

The pharmaceutical composition can be prepared using methods that are well known to the skilled in the art such as those contained in handbooks of pharmaceutical technology, such as the book *Remington The Science and Practice of Pharmacy,* 20th edition, Lippincott, Williams & Wilkins, Philadelphia, 2000 [ISBN: 0-683-306472].

The pharmaceutical compositions suitable for the use according to the present invention are all those appropriate for being administered either orally or topically.

In one embodiment of the invention, the pharmaceutical composition is a composition suitable for oral administration. Any pharmaceutical form suitable for oral administration is included within the use according to the object of the present invention, preferably solid compositions in powder or granulate form, or either liquid, in solution, suspension or syrup form, for example.

Preferably, the pharmaceutical composition for oral administration is in powder or granulate form. More preferably, it is in powder form.

In another embodiment of the invention, the pharmaceutical composition is a composition appropriate for topical administration. Any pharmaceutical form suitable for topical administration is included within the use according to the object of the present invention, either in a solid, liquid or semisolid form. Solid compositions for topical administration are generally in powder form, and may include a suitable carrier, such as talc, silica or microcrystalline cellulose, among others. The liquid compositions suitable for topical administration can be prepared by dissolving or dispersing the casein hydrolysate in a suitable carrier such as, for example, water, alcohols, glycols, or mixtures thereof, and are, for example, lotions, liniments, or tinctures; or else this liquid composition can be used to impregnate a support in the form of dressing or bandage that is applied to the affected area, or alternatively the liquid composition can be sprayed onto the affected area using pump sprayers or aerosols. Other forms of topical administration are semisolid compositions such as creams, gels, ointments or pastes.

Preferably, the pharmaceutical composition for topical administration is in the form of a cream, gel, ointment or paste.

The pharmaceutically acceptable excipients that can be used for preparing pharmaceutical compositions in solid form are well known to those skilled in the art and include, for example, diluents such as calcium carbonate, sodium carbonate, magnesium carbonate, magnesium oxide, calcium sulfate, calcium phosphate, sodium chloride, microcrystalline or powdered cellulose, cellulose acetate, ethyl cellulose, dextrates, dextrins, dextrose, lactose, lactitol, fructose, sorbitol, sucrose, maltodextrins, maltose, glyceryl palmitostearate, kaolin, polymethacrylates, pregelatinized starch or starch, among others, and mixtures thereof; lubricants, such as calcium stearate, magnesium stearate, talc, stearic acid, glyceryl behenate, glyceryl palmitostearate, sodium benzoate, sodium lauryl sulfate, sodium stearyl fumarate, or hydrogenated castor oil, among others, and mixtures thereof; disintegrants such as alginic acid, sodium croscarmellose, crospovidone, sodium starch glycolate, starch, low-substituted hydroxypropylcellulose, among others, and mixtures thereof; binding agents such as sodium carboxymethylcellulose, cellulose acetate phthalate, dextrates, dextrin, ethylcellulose, guar gum, maltodextrin, methylcellulose, microcrystalline cellulose, povidone, pregelatinized starch, stearic acid, or sucrose, among others, and mixtures thereof; anticaking agents such as tribasic calcium phosphate, calcium silicate, colloidal silica, magnesium silicate, magnesium trisilicate or talc, among others, and mixtures thereof; thickening agents such as colloidal silica, dextrin, ethylcellulose, hydroxyethyl cellulose, hydroxyethylmethyl cellulose, hypromellose, polyethylene glycol, trehalose, xanthan gum, among others, and mixtures thereof; suspending agents such as xanthan gum, guar gum, alginic acid, bentonite, carbomers, sodium or calcium carboxymethylcellulose, hydroxyethyl cellulose, hydroxypropyl cellulose, hydroxypropylmethyl cellulose, hydroxypropyl alginate, microcrystalline or powdered cellulose, anhydrous colloidal silica, dextrins, gelatins, kaolin, magnesium aluminum silicate, maltitol, povidone, sorbitan esters, or tragacanth, among others, and mixtures thereof; stabilizing agents such as guar gum, xanthan gum, alginic acid, ascorbic acid, calcium stearate, sodium carboxymethylcellulose, calcium carboxymethylcellulose, ethylcellulose, lecithin, monoethanolamine, potassium chloride, povidone, sorbitol, or xylitol, among others, and mixtures thereof; flavoring agents such as maltol, vanillin, ethyl vanillin, menthol, citric acid, fumaric acid, ethyl maltol, tartaric acid, peppermint, artificial or natural fruit aromas, among others, and mixtures thereof; sweetening agents such as sorbitol, maltitol, mannitol, dextrose, maltose, xylitol, saccharin, sucrose, sucralose, aspartame, acesulfame potassium, or trehalose, among others, and mixtures thereof; coloring agents such as curcumin, lactoflavin, iron oxides (red, yellow or black), caramel, lactoflavin phosphate, cochineal red, titanium dioxide, or carotenes, among others, and mixtures thereof; or mixtures thereof.

Some of the excipients and carriers suitable to be used in the liquid formulations, in the form of solutions, or suspensions are, for example, solvents such as water, alcohol, almond oil, castor oil, glycerin, among others; buffering agents such as diethanolamine, dibasic sodium phosphate, monobasic sodium phosphate, potassium citrate, sodium bicarbonate, sodium citrate dihydrate, among others, and mixtures thereof; viscosity modifiers such as alginic acid, bentonite, carbomers, carrageenan, gelatin, glycerin, hydroxyethyl cellulose, hydroxyethylmethyl cellulose, hydroxypropyl cellulose, maltodextrin, polyvinyl alcohol, sodium alginate, tragacanth, arabic gum, or xanthan gum, among others and mixtures thereof; emulsifying agents such as calcium stearate, cetyl alcohol, ethylene glycol palmitostearate, glyceryl monostearate, lecithin, oleic acid, poloxamers, sodium lauryl sulfate, sorbitan esters, polyoxyethylene castor oil derivatives, or emulsifying wax, among others, and mixtures thereof; suspending agents such as xanthan gum, guar gum, alginic acid, bentonite, carbomers, sodium or calcium carboxymethylcellulose, hydroxyethyl cellulose, hydroxypropyl cellulose, hydroxypropylmethyl cellulose, hydroxypropyl alginate, microcrystalline or powdered cellulose, anhydrous colloidal silica, dextrins, gelatins, kaolin, magnesium aluminum silicate, maltitol, povidone, sorbitan esters, or tragacanth, among others, and mixtures thereof; flocculating agents such as sodium acetate, sodium phosphate, sodium citrate, sodium lauryl sulfate, starch, alginates, tragacanth, or carbomers, among others, and mixtures thereof; wetting agents as benzalkonium chloride, sodium docusate, sodium lauryl sulfate, sorbitan esters, polyoxyethylene stearates or polyoxyethylene sorbitan fatty acid esters, among others, and mixtures thereof; preservatives such as benzalkonium chloride, benzyl alcohol, bronopol, parabens, sodium benzoate, sodium propionate, sorbic acid or thimerosal, among others, and mixtures thereof; flavoring agents as maltol, vanillin, ethyl vanillin, menthol, citric acid, fumaric acid, ethyl maltol, tartaric acid, peppermint, artificial or natural fruit aromas, among others, and mixtures thereof; sweetening agents such as sorbitol, maltitol, mannitol, dextrose, maltose, xylitol, saccharin, sucrose, sucralose, aspartame, acesulfame potassium or trehalose, among others, and mixtures thereof; coloring agents such as curcumin, lactoflavin, iron oxides (red, yellow or black), caramel, lactoflavin phosphate, cochineal red, titanium dioxide, or carotenes, among others, and mixtures thereof; or mixtures thereof.

The semisolid topical formulations in the form of creams, gels, ointments or pastes comprise a pharmaceutically acceptable carrier in which the casein hydrolysate is dissolved, emulsified, dispersed or suspended. This carrier is selected from water, a non-aqueous water miscible carrier, such as for example ethanol or isopropanol, and a non-aqueous water-immiscible carrier, such as for example paraffin oil. Optionally, such semisolid compositions for topical administration contain a pharmaceutically acceptable excipient such as, for example, surfactant and emulsifier agents, lipidic and emollient compounds, consistency factors and thickening agents, stabilizers, hydrotropes, preservative agents, essences, coloring agents, silicone compounds, fats, waxes, lecithins, phospholipids, UV sun protection factors, or mixtures thereof.

The excipients suitable to be used in the pharmaceutical compositions of the present invention are well known to those skilled in pharmaceutical technology and are described, for example, in the book R. C. Rowe, P. J. Sheskey and P. J. Weller, *Handbook of Pharmaceutical Excipients*, Fourth Edition, Pharmaceutical Press, 2003.

In a preferred embodiment, the pharmaceutical composition is in the form of powder or granulate for oral use. The powder is usually prepared by mixing the casein hydrolysate in powder form with at least one pharmaceutically acceptable excipient. The granulate consists of powder particles that have been aggregated to form larger particles, and it is prepared according to procedures which are well known to those skilled in the art, such as dry granulation or wet granulation.

The compositions in the form of powder or granulate are usually taken after dissolution or dispersion in water or another liquid.

In one embodiment of the invention, the powder or granulate composition is presented in a bulk container as, for example, in a glass container with a wide opening, so that the required dose for each administration is taken as needed, preferably with the help of a measurement device or dispenser to measure the dose to be administered.

In another embodiment of the invention, the powder or granulate composition is presented in the form of monodose sachets, containing the unit dose suitable for oral administration. Those sachets can be made of paper or either of aluminium or plastic laminates. Preferably, the oral unit dose comprises between 4 and 8 g of the casein hydrolysate, more preferably between 5 and 7 g, and still more preferably about 6 g of the hydrolysate.

In a particularly preferred embodiment of the invention, the composition for oral use is in powder form. More preferably, the composition in powder form comprises the casein hydrolysate, and a pharmaceutically acceptable excipient which is selected from sweeteners, flavouring agents and coloring agents, or mixtures thereof.

Preferably, the composition in powder form contains a quantity of the casein hydrolysate ranging between 70% and 99%, and more preferably ranging between 80% and 95%, expressed as weight ratio relative to the total weight of the composition.

In another preferred embodiment of the invention, the pharmaceutical composition according to the use of the present invention is a composition for topical administration, preferably in the form of cream, gel, ointment or paste. Preferably, this composition for topical administration comprises an amount of the casein hydrolysate ranging between 5% and 25%, and more preferably ranging between 7% and 15%.

It is also a part of the object of the present invention a pharmaceutical composition comprising a casein hydrolysate and at least one pharmaceutically acceptable excipient and/or carrier, characterized in that the composition is in the form of cream, gel, ointment or paste for topical administration, wherein this casein hydrolysate comprises peptides wherein the molar fraction of peptides carrying a carboxy terminal proline, expressed in %, is more than two times the molar fraction of proline, expressed in %, in the casein substrate used to generate the hydrolysate. Preferably, this composition for topical administration contains an amount of the casein hydrolysate ranging between 5% and 25%, and more preferably ranging between 7% and 15%, expressed in weight.

Creams, as it is well known to those skilled in pharmaceutical technology are semisolid emulsions, which can be of the oil-in-water (o/w) type or water-in-oil (w/o) type, formulated from an oil phase, an aqueous phase and an emulsifying agent. The oil phase consists of a carrier which can be, for example, liquid paraffin or a vegetable oil such as, for example, castor oil, almond oil, peanut oil, sesame oil, cottonseed oil or corn oil.

Gels are obtained from a liquid that is gelled by adding a rheological agent or a gelling agent. Some of the gelling agents suitable to be used in the present invention are, for example, carrageenan, guar gum, tragacanth gum, locust bean gum, pectin, agar, alginic acid, carbomers, carboxymethylcellulose, methylcellulose, hydroxyethyl cellulose, hydroxypropylmethyl cellulose, and polyethylene glycol, among others.

Ointments are semisolid fat preparations, which contain the active ingredient dissolved or in dispersed form. Ointments can be formulated with various vehicles such as paraffin, plastibases (a mixture of polyethylene with a series of hydrocarbons), vegetable oils, such as peanut oil, sesame oil, olive oil, cottonseed oil, almond oil, corn oil, silicones or polyethylene glycols, among others, or with a mixture thereof.

Pastes are prepared analogously to the ointments, and they show a more solid consistency since they contain greater amounts of insoluble solids.

Next, some examples are provided with the purpose of illustrating the invention, but not limiting it.

EXAMPLES

Example 1.—Preparation of a Composition in Powder Form

A composition in powder form was prepared using the following components:

| Ingredient | Weight (g/unit dose) | % (weight) |
| --- | --- | --- |
| Casein hydrolysate | 6 | 91.58 |
| Sucralose | 0.050 | 0.76 |
| Lemon flavor | 0.50 | 7.63 |
| Coloring agent | 0.002 | 0.03 |

All ingredients were thoroughly mixed until obtaining a homogeneous mixture and said mixture was introduced into a monodose sachet.

Each monodose sachet contained 6 g of casein hydrolysate.

Example 2.—Preparation of a Composition in Cream/Lip Balsam Form

A composition in a cream form was prepared using the following components:

| Ingredient | % (weight) |
|---|---|
| Casein hydrolysate | 10.00 |
| Aroma | 1.00 |
| Emulsifier | 5.00 |
| Waxes | 15 |
| Water | q.s. |

The composition was prepared following procedures that are well known to the skilled in the art.

Example 3.—Efficacy Study in Herpes Labialis

The efficacy of the orally administered casein hydrolysate was tested for the treatment and prevention of herpes labialis.

12 patients suffering from herpes labialis (7 men and 5 women) were treated, their ages comprised between 17 and 56 years. This patient group periodically presented outbreaks of the disease, with a frequency ranging between 3 and 12 per year, with an average of 7.2 outbreaks per year for this group. During the treatment, 2 monodose sachets of the powder product prepared in Example 1 were administered daily, containing 6 g of the protein hydrolysate in each sachet.

In all the cases, the product was effective for the treatment of herpes labialis, so that after 2 to 3 days of treatment, the complete remission of the symptoms was achieved for all the patients.

Once the symptoms had disappeared, 8 of these patients continued to take one monodose sachet of the product daily, as a maintenance dosage regimen to prevent the appearance of further outbreaks of the infection, for a period of time comprised between 13 and 24 months, depending on the case. In all cases it was managed to avoid the appearance of new outbreaks of herpes labialis, during the maintenance dosage regimen.

Example 4.—Efficacy Study in Genital Herpes

In this example, the efficacy of the orally administered casein hydrolysate was tested for the treatment and prevention of genital herpes.

6 patients suffering from genital herpes (3 men and 3 women) were treated, their ages comprised between 19 and 42 years. During the treatment, 3 sachets of the powder product prepared in Example 1 were administered daily, containing 6 g of the protein hydrolysate in each sachet. In all cases, the complete cure of the symptoms of genital herpes was achieved after from 4 to 6 days of treatment.

After the remission of the symptoms, the patients continued taking 1 monodose sachet of the product daily for 12 and 18 months and with this dosage no new outbreaks of the disease were observed. Therefore, the product was also effective for the prevention of new episodes of genital herpes.

Example 5.—Efficacy Study in Herpes Zoster

The efficacy of the orally administered casein hydrolysate was tested for the treatment and prevention of herpes zoster. In this study the monodose sachets of the powder product prepared in Example 1 were also employed.

5 patients suffering from herpes zoster (2 men and 3 women) were treated, their ages comprised between 39 and 80 years, and presenting affectation in the back, or in the abdomen, or in the legs and the abdomen.

The administration of 4 sachets of the product daily allowed the healing of the symptoms after 4 or 5 days of treatment, for all the patients of the study.

The patients continued for 12 and 18 months in a preventive dosage regimen, with a daily sachet of the product, thereby a decrease in the number of recurrences of herpes zoster was observed, as well as a decrease in their virulence, for all patients of the study.

The invention claimed is:

1. A method for treatment of infections caused by herpesvirus and/or decreasing the number of recurrences of infection in treated patients comprising administering to a patient suffering from herpes a casein hydrolysate, wherein the hydrolysate comprises peptides wherein the molar fraction of peptides carrying a carboxy terminal proline, expressed in %, is more than two times the molar fraction of proline, expressed in %, in the casein substrate used to generate the hydrolysate, and wherein the casein hydrolysate is administered orally according to a daily dose between 4 and 40 g.

2. The method according to claim 1, wherein the molar fraction of the peptides in the hydrolysate carrying a carboxy terminal proline, expressed in %, is at least three times the molar fraction of proline, expressed in %, in the casein substrate used to generate the hydrolysate.

3. The method according to claim 1, wherein the average length of the peptides in the casein hydrolysate is between 3 and 9 amino acids.

4. The method according to claim 1, wherein the molar fraction of peptides carrying a carboxy terminal proline in the casein hydrolysate is at least 25%.

5. The method according to claim 4, wherein the molar fraction of peptides carrying a carboxy terminal proline in the casein hydrolysate is between 30% and 70%.

6. The method according to claim 1, wherein the infections are caused by herpesviruses selected from the group consisting of herpes simplex type 1, herpes simplex type 2, varicella zoster virus, Epstein-Barr virus, cytomegalovirus, herpesvirus type 6, herpesvirus type 7, and Kaposi's Sarcoma herpesvirus.

7. The method according to claim 6, wherein the herpesvirus is selected from the group consisting of herpes simplex type 1, herpes simplex type 2 and varicella zoster virus.

8. The method according to claim 1 wherein the herpesvirus infection is selected from the group consisting of herpes labialis, genital herpes, and herpes zoster.

9. The method according to claim 1, wherein a unit oral dose of between 4 and 8 g of the casein hydrolysate is used, which is administered from 1 to 5 times daily.

10. The method according to claim 1, wherein the casein hydrolysate is administered in the form of a pharmaceutical composition suitable for oral administration comprising a pharmacologically effective amount of the hydrolysate and at least one pharmaceutically acceptable excipient and/or carrier.

11. The method according to claim 10, wherein the pharmaceutical composition is in powder or granulate form.

12. The method according to claim 11, wherein the composition is dosed in monodose sachets containing between 4 and 8 g of the casein hydrolysate.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Arg Lys Asp Val Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Tyr Gly Ala Val Val Asn Asp Leu
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Tyr Ala Gly Ala Val Val Asn Asp Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Tyr Ala Gly Ala Val Val Asn Asp Leu
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Val Val Asn Asp Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Ala Pro Gly Asp Glu Pro Ala Pro Pro Tyr
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Residue 1 = D-Ala
<220> FEATURE:
<221> NAME/KEY: MOD_RES
<222> LOCATION: (8)..(8)
<223> OTHER INFORMATION: Residue 8 = amide

<400> SEQUENCE: 7

Ala Ser Thr Thr Thr Asn Tyr Thr
1               5

<210> SEQ ID NO 8
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 8

Ala Ser Thr Thr Thr Asn Tyr Thr
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Residue 1 = D-Ala

<400> SEQUENCE: 9

Ala Ser Thr Thr Thr Asn Tyr Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Residue 1 = D-Ala

<400> SEQUENCE: 10

Ala Ala Ser Ser Ser Asn Tyr Met
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Thr Asp Asn Tyr Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide

<400> SEQUENCE: 12

Thr Thr Ser Tyr Thr
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Thr Thr Asn Tyr Thr
```

```
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(9)
<223> OTHER INFORMATION: Residues 1-9 = D amino acids

<400> SEQUENCE: 14

Arg Lys Lys Arg Arg Gln Arg Arg Arg
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(9)
<223> OTHER INFORMATION: Residues 1-9 = D amino acids

<400> SEQUENCE: 15

Arg Arg Arg Arg Arg Arg Arg Arg Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(9)
<223> OTHER INFORMATION: Residues 1-9 = D amino acids

<400> SEQUENCE: 16

Arg Arg Arg Gln Arg Arg Arg Arg Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Residue 7 = amino acid with chiral center

<400> SEQUENCE: 17

Arg Arg Trp Trp Cys Arg Xaa
1               5

<210> SEQ ID NO 18
<211> LENGTH: 20
<212> TYPE: PRT
<213> ORGANISM: Artificial Sequence
<220> FEATURE:
<223> OTHER INFORMATION: Synthetic sequence

<400> SEQUENCE: 18
```

```
Ile Glu Leu Val Phe Thr Gly Val Leu Ala Gly Val Trp Gly Glu Gly
1               5                   10                  15

Gly Lys Phe Val
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19

Arg Arg Lys Lys Ala Ala Val Ala Leu Leu Pro Ala Val Leu Leu Ala
1               5                   10                  15

Leu Leu Ala Pro
            20

<210> SEQ ID NO 20
<211> LENGTH: 35
<212> TYPE: PRT
<213> ORGANISM: Artificial Sequence
<220> FEATURE:
<223> OTHER INFORMATION: Synthetic peptide

<400> SEQUENCE: 20

Val Cys Val Leu Ala His His Phe Gly Lys Glu Phe Thr Pro Pro Val
1               5                   10                  15

Gln Ala Ala Tyr Gln Lys Trp Ala Gly Val Ala Asn Ala Leu Ala His
            20                  25                  30

Lys Tyr His
        35
```